(12) United States Patent
Weisskoff et al.

(10) Patent No.: US 6,969,507 B2
(45) Date of Patent: Nov. 29, 2005

(54) IMAGING SEXUAL RESPONSE

(75) Inventors: Robert M. Weisskoff, Lexington, MA (US); Stephen C. Knight, Cambridge, MA (US); Wayne Carter, Branford, CT (US)

(73) Assignee: Epix Pharmaceuticals, Inc., Cambridge, MA (US)

( * ) Notice: Subject to any disclaimer, the term of this patent is extended or adjusted under 35 U.S.C. 154(b) by 117 days.

(21) Appl. No.: 10/291,900

(22) Filed: Nov. 8, 2002

(65) Prior Publication Data

US 2003/0129135 A1 Jul. 10, 2003

Related U.S. Application Data

(62) Division of application No. 09/718,161, filed on Nov. 21, 2000, now Pat. No. 6,548,044.
(60) Provisional application No. 60/167,257, filed on Nov. 22, 1999.

(51) Int. Cl.[7] .......................... A61K 49/00; A61B 5/055
(52) U.S. Cl. .......................... 424/9.2; 424/9.1; 424/9.3
(58) Field of Search ................................ 424/9.3, 9.36, 424/9.365, 9.1, 9.2

(56) References Cited

U.S. PATENT DOCUMENTS

| | | |
|---|---|---|
| 5,649,537 A | 7/1997 | Anelli et al. |
| 5,707,605 A | 1/1998 | Meade et al. |
| 5,769,088 A | 6/1998 | Place |
| 6,037,346 A * | 3/2000 | Doherty et al. ........ 514/252.03 |
| 6,319,488 B1 | 11/2001 | Licha et al. |

FOREIGN PATENT DOCUMENTS

| | | |
|---|---|---|
| WO | WO-96/23526 | 8/1996 |
| WO | WO-98/20908 | 5/1998 |
| WO | WO-99/17809 | 4/1999 |

OTHER PUBLICATIONS

American Psychiatric Association, "Sexual Dysfunctions," *Sexual and Gender Identity Disorders: DSM–IV*™, pp. 493–538, 4th ed., Washington DC: American Psychiatric Association (1996).

Kaneko et al., "Sequential Contrast–Enhanced MR Imaging of the Penis," *Radiology*, 191(1), pp. 75–77 (1994).

Stehling et al, "Gadolinium–Enhanced Magnetic Resonance Angiography of the Pelvis in Patients with Erectile Impotence," *MAGMA*, 5, pp. 247–254 (1997).

\* cited by examiner

*Primary Examiner*—Michael Hartley
(74) *Attorney, Agent, or Firm*—Fish & Richardson P.C., P.A.

(57) ABSTRACT

The present invention relates to methods for contrast-enhanced imaging of sexual response. In particular, the present invention relates to methods of magnetic resonance imaging (MRI), computerized X-ray tomography (CT), ultrasound, and optical imaging using contrast agents to measure blood flow during sexual response, especially female sexual response. The invention relates to methods of analyzing normal sexual function and sexual dysfunction and provides a means for evaluating and screening potential therapeutic compounds for enhancing sexual function or treating sexual dysfunction.

16 Claims, 2 Drawing Sheets

Imaging Response to Visual Stimulus

IMAGING SEXUAL RESPONSE

CROSS-REFERENCE TO RELATED APPLICATIONS

This application is a divisional application of U.S. application Ser. No. 09/718,161, filed Nov. 21, 2000, now U.S. Pat. No. 6,548,044, which claims the benefit of U.S. Provisional Application No. 60/167,257, filed Nov. 22, 1999.

TECHNICAL FIELD OF THE INVENTION

The present invention relates to methods for contrast-enhanced imaging of sexual response. In particular, the present invention relates to methods of magnetic resonance imaging (MRI), computerized X-ray tomography (CT), ultrasound, and optical imaging using contrast agents to measure blood flow during sexual response, especially female sexual response. The invention relates to methods of analyzing normal sexual function and sexual dysfunction and provides a means for evaluating and screening potential therapeutic compounds for enhancing sexual function or treating sexual dysfunction.

BACKGROUND OF THE INVENTION

Diagnostic imaging techniques, such as magnetic resonance imaging (MRI), X-ray, nuclear radiopharmaceutical imaging including PET and SPECT, ultraviolet/visible/infrared light, and ultrasound, have been used in medical diagnosis for a number of years. In some cases, contrast media improves the image quality or provides specific additional useful information.

The contrast agent must interfere with the wavelength of electromagnetic radiation used in the imaging technique, alter the physical properties of tissue to yield an altered signal, or, as in the case of radiopharmaceuticals, provide the source of radiation itself. Commonly used imaging materials include organic molecules, metal ions, salts or chelates, particles (particularly iron particles), or labeled peptides, proteins, polymers or liposomes. After administration, the agent may non-specifically diffuse throughout body compartments prior to being metabolized and/or excreted; these agents are generally known as non-specific agents. Alternatively, the agent may have a specific affinity for a particular body compartment, cell, organ, or tissue; these agents can be referred to as targeted agents.

In recent years, a number of contrast agents have been developed that may be used to enhance imaging of the blood pool. See, e.g., WO 96/23526, herein incorporated by reference in its entirety. Such diagnostic imaging contrast agents may comprise an image-enhancing moiety, a plasma protein binding moiety and a blood half-life extending moiety and exhibit improved blood retention. Although a number of methods using such contrast agents have been described, prior to this application it was not known if normal sexual function or sexual dysfunction could be measured with such types of agents.

The Diagnostic and Statistical Manual of Mental Disorders, 4th edition, Washington D.C., American Psychiatric Association, 1996 (DSM-IV, herein incorporated by reference) describes a number of sexual dysfunctions. These include sexual desire disorders such as hypoactive sexual desire disorder and sexual aversion disorder; sexual arousal disorders such as female sexual arousal disorder and male erectile disorder; orgasmic disorders such as female orgasmic disorder (formerly, inhibited female orgasm), male orgasmic disorder (formerly, inhibited male orgasm), and premature ejaculation, dyspareunia, vaginismus and sexual dysfunction not otherwise specified. The DSM-IV describes several subtypes that apply to primary sexual dysfunctions including lifelong type, acquired type, generalized type, situational type, and sexual dysfunction due to psychological factors or due to combined factors. Sexual dysfunction may also be due to general medical condition or may be substance induced, such as by alcohol, antidepressants and antihypertensives.

A number of compounds have been described to treat sexual dysfunction. For instance, Viagra™ (sildenafil citrate, Pfizer, Inc.) has been used to treat male erectile disorder. Physiologically, sexual stimulation causes local release of nitric oxide (NO) in the corpus cavernosum. NO then activates the enzyme guanylate cyclase, which results in increased levels of cGMP, producing smooth muscle relaxation in the corpus cavernosum and allowing inflow of blood. Sildenafil citrate enhances the effect of NO by specifically inhibiting PDE5, which is responsible for degradation of cGMP in the corpus cavernosum.

Female sexual arousal disorder is a poorly understood condition for which there is no reliable diagnostic test. The underlying pathophysiology of this condition is thought to include an inadequate vascular arousal response to sexual stimulation. Vaginal photoplethysmography is the most widely reported method for assessing the vascular component of the arousal response to sexual stimulation (by measuring a change in vaginal pulse amplitude). However, vaginal photoplethysmography has the disadvantage of not providing an absolute measure of either vaginal blood volume or blood flow because all changes are observed without a quantifiable reference baseline. Furthermore, photoplethysmography results are highly variable and depend on exact placement of the probe, among other parameters. Thus, there remains a need to develop better methods and techniques for measuring blood flow in sexual response, preferably female sexual response, and, more particularly, in female sexual arousal disorders.

SUMMARY OF THE INVENTION

In one embodiment, the instant invention provides a method for contrast-enhanced diagnostic imaging of normal sexual function or sexual dysfunction. In a preferred embodiment, MRI, ultrasound, computed X-ray tomography (CT), or optical imaging is used to image sexual dysfunction. In a more preferred embodiment, the sexual dysfunction is a female sexual arousal disorder.

In another embodiment, the instant invention provides a method for measuring the therapeutic effect of a compound on sexual dysfunction. In a preferred embodiment, MRI or optical imaging is used to measure the effects of the therapeutic compounds. In another preferred embodiment, the sexual dysfunction treated is female sexual arousal disorder. In an even more preferred embodiment, the compound tested is sildenafil citrate (Viagra™).

In another embodiment, the instant invention provides a method for screening for potential therapeutic compounds for efficacy in the treatment of sexual dysfunction. In a preferred embodiment, the compounds are screened for treating female sexual arousal disorder. In another preferred embodiment, MRI or optical imaging is used to screen the compounds.

Figure 1:
FIG. 1 shows by MRI using contrast agent MS-325 a time course of normal female sexual arousal.
Figure 1:

The top left-hand panel of FIG. 1 shows an MRI image before administration of MS-325.

The top middle and right-hand panel of FIG. 1 show MRI images during administration of MS-325 while the female subject watches neutral video.

The bottom three panels of FIG. 1 show MRI images during administration of MS-325 while the female subject watches erotic video.

Figure 2:
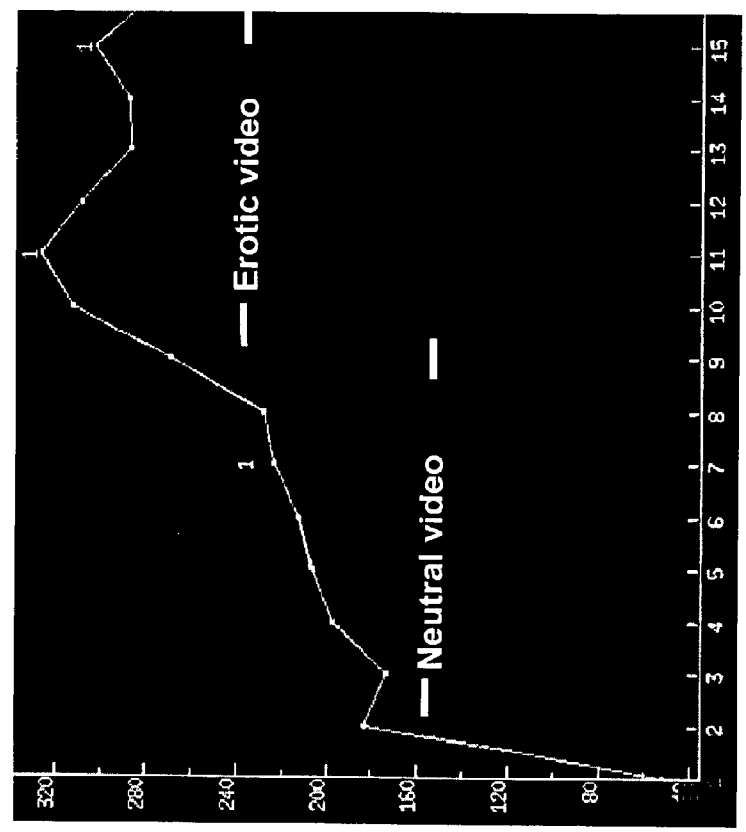
Figure 2:

FIG. 2, left panel, shows the blood flow image area ("Region of Interest" or ROI) that is quantitated (labeled with a box and number).

FIG. 2, right panel, shows a graph in which the signal intensity of the quantitated image area, as shown in FIG. 2, left panel, is plotted against time.

DETAILED DESCRIPTION OF THE INVENTION

In order that the invention herein described may be more fully understood, the following detailed description is set forth.

A. Definitions

As used herein, the term "sexual dysfunction" encompasses those disorders including those defined by the DSM-IV, and includes, without limitation, sexual desire disorders such as hypoactive sexual desire disorder and sexual aversion disorder; sexual arousal disorders such as female sexual arousal disorder and male erectile disorder; orgasmic disorders such as female orgasmic disorder (formerly, inhibited female orgasm), male orgasmic disorder (formerly, inhibited male orgasm), and premature ejaculation, dyspareunia, vaginismus and sexual dysfunction not otherwise specified. In a preferred embodiment, the sexual dysfunction is a sexual arousal disorder. In an even more preferred embodiment, the sexual dysfunction is female sexual arousal disorder. The etiology may be psychogenic, anatomical, or pathophysiological.

The term "diagnostic medical imaging", or simply "medical imaging" or "diagnostic imaging" refers to a method of graphically or pictorially investigating an animal or human body for the purposes of studying the body's anatomy or physiology or an abnormality thereof. Generally, medical imaging is conducted by a radiologist or someone under his or her supervision. Typical methods of medical imaging which are contemplated by the present invention include, among others, computerized X-ray tomography (CT), ultrasound, magnetic resonance imaging (MRI), and optical imaging.

As used herein, the term "contrast agent" comprises those agents that enhance image contrast during diagnostic imaging. In a preferred embodiment, a contrast agent is one that enhances contrast in MRI or optical imaging. In another preferred embodiment, the contrast agent is one that enhances blood flow/blood pool imaging in MRI or optical imaging. In a more preferred embodiment, the contrast agent is one that exhibits improved blood retention and comprises an image-enhancing (or signal-generating) moiety (IEM), a plasma protein binding moiety (PPBM) and a blood half-life extending moiety (BHEM). See, e.g., WO 96/23526, supra. In an even more preferred embodiment, the contrast agent is MS-325 (MS-325, EPIX Medical, Inc.; see, e.g., WO 96/23526) or MultiHance™ (Bracco Pharmaceuticals, Inc.). Other MRI contrast agents that are suitable for use in the invention include Magnevist™ (Schering AG), ProHance™ (Bracco Pharmaceuticals, Inc.), Gadomer-17 (Schering AG), B22956/1 (Bracco Pharmaceuticals, Inc.) and the contrast agents disclosed in U.S. Pat. No. 5,649,537, MP-2269 (Mallinckrodt, Inc.) and the contrast agents disclosed in international patent application (PCT) WO 98/20908, P760 and P775 (Guerbet SA), Clariscan™ (Nycomed Amersham), Combidex™ and Ferridex™ (Advanced Magnetics, Inc.), gadolinium texaphrin (Pharmacyclics, Inc.), and Eovist (Schering AG). Contrast agents for use in ultrasound imaging of sexual response include SHU-555c (Schering AG), AI-700 (Acusphere, Inc.), NC-100100 (Nycomed Amersham), Sonovist™ (Schering AG), Optison™ and Albunex™ (Molecular Biosystems, Inc.), and Echogen™ (Sonus Pharmaceuticals, Inc.). Contrast agents for use in CT include iohexol, iopamidol, iopromide, iopentol, and ioxaglate. Contrast agents that have affinities for endogenous blood components, especially human serum albumin, are particularly preferred. Contrast agents for use in optical imaging include indocyanine green and those disclosed in international patent application (PCT) WO 97/13490.

B. Method for Measuring Physiological Sexual Response

In one aspect, the present invention provides a method for accurately monitoring normal sexual function or sexual dysfunction in a subject. In particular, the invention provides a diagnostic imaging method that involves the use of a contrast agent that measures one or more parameters of sexual function. The use of the contrast agents allow for "real-time" monitoring and quantifying sexual function. In a preferred embodiment, the invention provides a diagnostic imaging method comprising the use of a contrast agent to measure and quantify female sexual arousal. The imaging methods useful in this invention are MRI, including magnetic resonance spectroscopy techniques, ultrasound, computerized X-ray tomography (CT), and optical imaging.

The contrast agent is preferably a blood pool (also known as blood flow) contrast agent. Furthermore, the contrast agent is preferably administered by intravenous or intra-arterial injection so that the amount of contrast agent in the blood is high relative to the amount of contrast agent in the interstitium or within cells. Contrast agents which extravasate slowly, examples of which are MS-325, Gadomer-17, and P760, are preferred. Medical imaging and testing should be conducted shortly after administration of the contrast agent. As time progresses, the contrast agent may extravasate and reduce the amount of contrast between blood and tissue, or it may be excreted. In the case of MS-325, imaging and testing may be conducted up to one hour after administration. When Magnevist™ is employed, the time window is 30 minutes.

The method for contrast-enhanced diagnostic imaging of normal sexual function or sexual dysfunction comprises the steps of:

(a) administering a contrast agent to a subject;

(b) subjecting the subject to diagnostic medical imaging complementary to said contrast agent's intended use;

(c) measuring an imaging signal characteristic of the contrast agent;

(d) subjecting the subject to a stimulus; and (e) monitoring an imaging signal characteristic of the contrast agent to assess the sexual function after stimulus.

The steps (b) through (e) of the method may be repeated several times if sufficient contrast agent is still present in the blood of the body. The contrast agent may be re-administered, i.e. step (a) may be repeated, if the method is to be repeated, and the contrast agent's effect has diminished substantially. One skilled in the art will readily recognize if enough contrast agent is circulating within the body and if more should be administered.

Several regions of the body may be imaged, including the head, legs, pelvic area, and torso. The region preferably comprises the brain, spine, central nervous system (CNS) or other nervous system of the subject, and more preferably the pelvis or genitalia of the subject.

In a preferred embodiment, the contrast agent is a blood pool or blood flow contrast agent. In a more preferred embodiment, the contrast agent is one capable of enhancing blood flow or blood pool contrast in MRI or optical imaging. Suitable blood pool contrast agents include those described in WO 96/23526.

In a preferred embodiment, the sexual function that is assessed is sexual arousal and the stimulus is one designed to cause sexual arousal, including somatosensory, audiovisual, physical, and pharmacological stimuli. In a more preferred embodiment, the stimulus is one that causes sexual arousal in women without sexual dysfunction.

In one preferred embodiment of the method of measuring sexual response in women, the relative size of the clitoris is determined with and without stimulation. In this embodiment, the diagnostic imaging method is MRI and the size of the clitoris is measured by counting the number of pixels comprising the clitoris in steps (c) and (e). An increase in the number of pixels is equivalent to an increase in the size of the clitoris where all other MRI imaging and data processing parameters are the same. An increase in the size of clitoris is indicative of sexual arousal. The relative size of the clitoris in steps (c) and (e) of the method may also be determined by CT by counting the number of voxels comprising the clitoris.

In an alternative embodiment, the sexual response of women is determined by measuring the relative increase in blood volume to the clitoris. In the above method, the patient is administered MS-325 in step (a). In step (c), a region of interest (ROI) within the clitoris is selected and the signal measured prior to administration of contrast agent. A region of interest within an easily imaged major blood vessel is also selected as an internal standard against which blood flow is calculated. The femoral artery or vein is most preferred. The MRI signal in this artery is also determined before contrast agent administration. Contrast agent is administered at time equals zero and signal intensity data from the two ROIs are collected regularly for approximately five to ten minutes during which time the subject is not exposed to the sexual stimulus. Stimulation is then applied, and image data acquisition from the two ROIs is continued. The data from the two ROIs are used to calculate a relative blood volume within the clitoral ROI according to the following formula:

$$BV(t)=[S_c(t)-S_c(0)]/[S_a(t)-S_a(0)],$$

where t is time, BV(t) is the relative blood volume within the clitoral ROI at time t, $S_c(t)$ and $S_c(0)$ are the average MRI signals within the clitoral ROI at time t and immediately before contrast agent administration respectively, and $S_a(t)$ and $S_a(0)$ are the average MRI signals within the reference artery ROI at time t and immediately before contrast agent administration respectively. The BV(t) data are then fit to the following curve:

$$BV(t)=C1+C2 \cdot t+C3 \cdot E(t),$$

where C1, C2, and C3 are fitted constants and E(t) is a function that equals zero for times, t, when sexual stimulus is absent, and equals unity when sexual stimulus is applied. The ratio C3/C1 is an indicator of increase in relative blood volume upon stimulation. A statistical test, regression for example, may be conducted to reject the null hypothesis, C3=zero, within desired confidence limits, which indicates a complete lack of increase in blood flow, and therefore any physiological sexual response, upon stimulation. C2 is relative to the rate of extravasation of the contrast agent during the examination, and can be used to correct for extravasation of the agent if such occurs. The contrast agent MS-325 has a stable blood concentration over typical stimulation periods and is therefore a preferred contrast agent in this embodiment.

In another embodiment of this invention, the method is used to quantify normal sexual function in healthy human adults. In another embodiment of this invention, the method is used to measure sexual dysfunction. In a preferred embodiment of this invention, the technique is used to quantify the arousal response in healthy female volunteers. In another preferred embodiment, the technique is used to diagnose subjects with female sexual arousal disorder.

The invention may be practiced using subjects of either sex and of any age. The invention may be used to determine normal sexual function or may be used to study or diagnose sexual dysfunction by comparison to the mean of quantified arousal of normal subjects. Subjects are chosen depending upon the parameters of a particular study or clinical dysfunction presented. In an alternative embodiment, the invention may be practiced using animals to determine normal sexual function or sexual dysfunction, see infra.

For studies of female sexual arousal, subjects may include both pre-menopausal and post-menopausal women. Post-menopausal women may include those who use estrogen-replacement therapy and those who do not. Subjects may include those who have had disease or who have undergone surgery or trauma to any portion of the female reproductive system or genitalia; including those who have or who have had any type of sexually transmitted diseases (STDs). Such diseases include, without limitation, bacterial, viral or fungal infections; for example, Chlamydia, HIV, herpes, gonorrhea, syphilis, or other diseases affecting the reproductive organs. Other such diseases include, without limitation, endometriosis, diabetes, hypertension, endocrine disorders, or cancer of any of the reproductive organs. Surgery and trauma includes, without limitation, hysterectomy, ovarectomy, and surgery for removal of fibroid tumors or prolapsed uterus.

C. Therapy Assessment Methods

In another aspect, the instant invention provides a method for measuring the therapeutic effect of a compound on sexual dysfunction. The method comprises the steps of:

(a) administering a contrast agent to a subject;

(b) subjecting the subject to diagnostic medical imaging complementary to said contrast agent's intended use;

(c) measuring an imaging signal characteristic of the contrast agent to establish a baseline;

(d) subjecting the subject to a stimulus that will assess the sexual function;

(e) monitoring an imaging signal characteristic of the contrast agent to assess the sexual function after stimulus;

(f) administering an effective amount of a compound expected to provide a therapeutic effect on the sexual function; and (g) determining if the sexual function has been enhanced as a result of treatment with the compound.

Comparing the imaging data in the absence and in the presence of a candidate therapeutic compound gives an indication of its efficacy. In the above method, any of the steps may be repeated using the same subject. In a particularly preferred embodiment, this method is practiced on a population of subjects with a reproducible and predictable induced sexual impairment.

In a preferred embodiment, the contrast agent is a blood pool or blood flow contrast agent. In a more preferred embodiment, the contrast agent is one capable of enhancing blood flow or blood pool contrast in MRI or optical imaging. Suitable blood pool contrast agents include those described in WO 96/23526.

In a preferred embodiment, the sexual function that is assessed is sexual arousal and the stimulus is one designed to cause sexual arousal. In a more preferred embodiment, the stimulus is one that causes sexual arousal in women.

In a preferred embodiment, the therapeutic compound is one that enhances sexual arousal in a woman with female sexual arousal disorder. In a preferred embodiment, the therapeutic compound is one used to treat sexual arousal disorders in either men or women. The therapeutic compound may be sildenafil citrate (Viagra™) or other compounds used to treat male erectile dysfunction. Other drugs in development for the treatment of sexual dysfunction include Cialis™ (Eli Lilly and ICOS Corp.), Befar™ (NexMed), Vardenafil™ (Bayer), apomorphine (TAP Pharmaceuticals), Alprostadil™ (MacroChem), desmethylsibutramine (Sepracor), PT 14 and PT 141 (Palatin Technologies), SC-113 (Scotia Holdings), PNU-83757 (Pharmacia), NMI-187 (NitroMed), liposomal alprostadil (BioSphere and Harvard Scientific Corp.), and Amesergide™ (Eli Lilly).

D. Screening Methods for New Therapeutic Compounds

In another aspect, the instant invention provides a method for screening potential compounds to treat sexual dysfunction. The method comprises the steps of:

(a) administering a contrast agent to a non-human or human animal or animal subject;

(b) subjecting the subject to diagnostic medical imaging complementary to said contrast agent's intended use;

(c) measuring an imaging signal characteristic of the contrast agent to establish a baseline;

(d) subjecting the subject to a stimulus that will assess the sexual function;

(e) monitoring an imaging signal characteristic of the contrast agent to assess the sexual function after stimulus;

(f) administering a compound that is being tested to determine if it has an effect on the sexual function; and (g) determining if the sexual function has been modified as a result of treatment with the compound by comparing the results of steps (a)–(e) with those of step (f).

In a preferred embodiment, the contrast agent is a blood pool or blood flow contrast agent. In a more preferred embodiment, the contrast agent is one capable of enhancing blood flow or blood pool contrast in MRI or optical imaging. Suitable blood pool contrast agents include those described in WO 96/23526.

In a preferred embodiment, the sexual function that is assessed is sexual arousal and the stimulus is one designed to cause sexual arousal.

For non-human animal subjects, the stimulus may be any type of signal that elicits a sexual response. These stimuli may include auditory signals, e.g., recorded or live vocalizations; olfactory signals, e.g., pheromones or other distinctive signaling odors; sensory cues, such as genital manipulation including masturbation, or visual cues. Stimuli that elicit a sexual response are known in the art and may be adapted for use in this method.

In a preferred embodiment of this method, compounds are tested first for safety and efficacy in non-human animal subjects. After these preliminary studies, compounds that appear to be safe and efficacious in non-human animals are tested for safety and efficacy in human subjects. In another preferred embodiment, compounds that have been approved for use in humans for other indications may be tested using the method of this invention to determine whether they may be used to treat sexual dysfunction or to enhance sexual function.

E. Contrast Agent Dosages and Imaging

A number of different contrast agents may be used according to this invention. In general, the contrast agents will be water soluble. The contrast agents may also comprise a pharmaceutically acceptable salt. Examples of such salts are provided in WO 96/22526. Contrast agents may be administered by any method known in the art, such as those disclosed in WO 96/22526. Contrast agents may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. As discussed above, in a preferred embodiment, the contrast agent is administered intravenously.

Dosage depends on the sensitivity of the diagnostic imaging instrumentation, as well as the composition of the contrast agent. For example, for MRI imaging, a contrast agent containing a highly paramagnetic substance, e.g., gadolinium (III), generally requires a lower dosage than a contrast agent containing a paramagnetic substance with a lower magnetic moment, e.g., iron (III). Preferably, dosage will be in the range of about 0.001 to 1 mmol/kg body weight per day of the active metal-ligand complex. More preferably, dosage will be in the range of about 0.005 and about 0.2 mmol/kg body weight per day. In a more preferred embodiment, the dosage will be 0.01, 0.02, 0.03, 0.04, 0.05, 0.06, 0.07, 0.08, 0.09 or 0.10 mmol/kg body weight per day administered intravenously.

Those skilled in the art will readily determine an appropriate dosage based on the recommendation of the contrast agent manufacturer or supplier and the empirical ability to undertake the methods described herein. It should be understood, however, that a specific dosage regimen for any particular subject will also depend upon a variety of factors, including the age, body weight, general health, sex, diet, time of administration, rate of excretion, drug combination, and the judgment of the treating physician.

If the application of this invention is MR imaging, following administration of the appropriate dosage of the contrast agent, MR imaging is carried out. The choice of pulse sequence (inversion recovery, IR; spin echo, SE, echo planar, EPI; time-of-flight, TOF; turbo-flash; gradient echo, GE) and the values of the imaging parameters (echo time, TE; inversion time, TI; repetition time, TR; flip angel, etc.) will be governed by the diagnostic information sought. In general, if one desires to obtain $T_1$-weighted images, then TE should be minimized to maximize $T_1$-weighting. Conversely, if one desires to measure $T_2$, then TE should be greater than 30 milliseconds and the TR maximized or flip angle minimized to minimize competing $T_1$ effects. TI and TR are generally on the order of about 5–1000 and 2–1000 milliseconds, respectively.

In order that this invention may be more fully understood, the following examples are set forth. These examples are for the purpose of illustration only and are not to be construed as limiting the scope of the invention in any way.

EXAMPLE 1

Imaging of the genitalia was performed in four premenopausal and four post-menopausal healthy, sexually functional women subjects after administration of MS-325 (MS-325, EPIX Medical, Inc.). All volunteers signed an IRB-approved informed consent form for the study.

Six of the subjects received an intravenous injection of 0.05 mmol/kg of MS-325 and two received an intravenous injection of 0.02 mmol/kg of MS-325. Dynamic MRI (3D SPGR, 11/1.7/35°) of the perineum was performed on all subjects while they viewed videos containing first neutral material, then erotic material and finally neutral material via a fiberoptic audiovideo system. Each segment of neutral or erotic material was up to 15 minutes in length. Subjects also filled out questionnaires in response to the videos that had them subjectively rate their degree of sexual arousal.

Serial imaging was performed at least every 3 minutes, beginning just prior to contrast injection and continuing up to 45 minutes post injection. Signal intensity measurements over time were made of the vaginal wall and mucosa, clitoris, skeletal muscle, and femoral artery. Clitoral volume was measured at each time point. Relative regional blood volume was determined from signal intensity versus time curves and compared with subjective measures of arousal.

All subjects tolerated the procedure and all reported sexual arousal on subjective questionnaires. Baseline (unstimulated) MS-325 images revealed strong enhancement of the genitalia. When compared to a neutral stimulus, erotic stimulus produced significant increases in image enhancement, increases in clitoral blood volume (43%±5%) and in clitoral size (85%±5%). See FIGS. 1 and 2. In four subjects studied up to 10 minutes following termination of the erotic stimulus, these changes decreased, but did not return to baseline levels during the observation period.

In these studies, MRI was compared with vaginal photoplethysmography to confirm that MRI accurately assessed the vascular component of the arousal response.

EXAMPLE 2

Imaging of genitalia is performed on female subjects who have or who are suspected of having sexual arousal dysfunction. The subjects receive an intravenous injection of 0.01 to 0.1 mmol/kg of MS-325. Dynamic MRI is performed as described above while they are exposed to neutral material and then erotic material. In one embodiment, the subjects view videos containing first neutral material, then erotic material and finally neutral material via a fiberoptic audiovideo system. Subjects may fill out questionnaires in response to the erotic material to allow them to subjectively rate their degree of sexual arousal.

Serial imaging is performed as described above. Signal intensity measurements over time are made of the vaginal wall and mucosa, clitoris, skeletal muscle, and femoral vein. Clitoral volume is measured at each time point. Relative regional blood volume is determined from signal intensity versus time curves and compared with subjective measures of arousal.

The clitoral volume and size of the female subjects may be compared to those of sexually functional women who have been similarly tested. For instance, mean values can be determined to compare rates of blood flow or changes in clitoral volume between sexually functional subjects and those suspected of having sexual dysfunction. A lack of change in clitoral volume and size in the female subjects may be indicative of sexual arousal dysfunction.

EXAMPLE 3

Imaging is performed as described in Example 2. After a diagnosis of sexual arousal dysfunction has been made in a subject or group of subjects, a therapeutic compound for sexual arousal disorder is administered. The therapeutic compound may be one that is known to treat sexual arousal dysfunction or may be one that is being screened for its ability to treat sexual arousal disorder. In one embodiment, the therapeutic compound is Viagra™. After treatment with the therapeutic compound, imaging is performed again as described in Example 2. By comparing the change in clitoral blood volume and size before treatment to that after treatment, one may determine if the therapeutic compound is effective for treating sexual arousal disorder in a particular subject or group of subjects.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for assessing the effect of a compound on female sexual arousal disorder or female orgasmic disorder comprising:
   (a) administering a magnetic resonance imaging contrast agent to a female subject;
   (b) subjecting the subject to magnetic resonance imaging;
   (c) measuring an imaging signal characteristic of the contrast agent to establish a baseline;
   (d) subjecting the female subject to a stimulus designed to cause sexual arousal;
   (e) monitoring an imaging signal characteristic of the contrast agent to assess the female sexual arousal disorder or female orgasmic disorder after the stimulus;
   (f) administering a compound hypothesized to produce an effect on the female sexual arousal disorder of female orgasmic disorder to the female subject; and
   (g) determining if the female sexual arousal disorder or female orgasmic disorder has been affected as a result of administration of the compound.

2. The method according to claim 1, wherein the magnetic resonance imaging contrast agent is MS-325.

3. The method according to claim 1, wherein the compound hypothesized to produce an effect on the female sexual arousal disorder or female orgasmic disorder is selected from the group consisting of sildenafil citrate, tadalafil, and vardenafil.

4. The method according to claim 1 wherein the subject is a mammal.

5. The method according to claim 4 wherein the subject is a human.

6. The method according to claim 1, wherein said determining step comprises:
   (h) subjecting the female subject after said compound administration to a stimulus designed to cause sexual arousal;
   (i) monitoring an imaging signal characteristic of the contrast agent to assess the female sexual arousal disorder or female orgasmic disorder after the stimulus; and
   (j) comparing the imaging signal characteristics obtained in step (e) and step (i) to assess the effect of the compound on the female sexual arousal disorder or female orgasmic disorder.

7. The method of claim 1 or claim 6, wherein the imaging signal characteristic of the contrast agent is monitored in the pelvis of said female subject.

8. The method of claim 1 or claim 6, wherein the imaging signal characteristic of the contrast agent that is monitored includes monitoring the number of pixels in a given region of interest.

9. The method of claim 1 or claim 6, wherein the imaging signal characteristic of the contrast agent that is monitored includes monitoring the blood volume in a given region of interest.

10. The method of claim 1 or claim 6, wherein the stimulus designed to cause sexual arousal is selected from somatosensory, audiovisual, physical, and pharmacological stimuli.

11. The method of claim 1, wherein said female subject is pre-menopausal.

12. The method of claim 1, wherein said female subject is post-menopausal.

13. The method of claim 1, wherein said compound is a PDE5 inhibitor.

14. The method of claim 8, wherein said region of interest is the genitalia.

15. The method of claim 9, wherein said region of interest is the genitalia.

16. The method of claim 3, wherein said compound is sildenafil citrate.

* * * * *

UNITED STATES PATENT AND TRADEMARK OFFICE
CERTIFICATE OF CORRECTION

PATENT NO. : 6,969,507 B2  
APPLICATION NO. : 10/291900  
DATED : November 29, 2005  
INVENTOR(S) : Robert M. Weisskoff, Stephen C. Knight and Wayne Carter It is certified that error appears in the above-identified patent and that said Letters Patent is hereby corrected as shown below:

Column 10, line 38 (Claim 1), please delete "of" and insert --or--therefor.

Signed and Sealed this

First Day of August, 2006

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 6,969,507 B2 |
| APPLICATION NO. | : 10/291900 |
| DATED | : November 29, 2005 |
| INVENTOR(S) | : Robert M. Weisskoff et al. |

It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by (117) days Delete the phrase "by 117" and insert -- by 124 days--

Signed and Sealed this

Twenty-fourth Day of April, 2007

JON W. DUDAS
*Director of the United States Patent and Trademark Office*